United States Patent [19]

Wright

[11] Patent Number: 5,074,285
[45] Date of Patent: Dec. 24, 1991

[54] THERMAL APPLICATOR METHOD
[75] Inventor: Sonja J. Wright, Sewickley, Pa.
[73] Assignee: Wright Linear Pump, Inc., Imperial, Pa.
[21] Appl. No.: 438,116
[22] Filed: Nov. 20, 1989
[51] Int. Cl.⁵ .......................... A61H 9/00; A61F 7/00
[52] U.S. Cl. .................................. 128/24.1; 128/402; 128/40; 128/82.1
[58] Field of Search ................. 128/400, 402, 24.1, 128/40, 82.1, 66, 87, 399, 691; 165/46

[56] References Cited

U.S. PATENT DOCUMENTS

| | | | |
|---|---|---|---|
| 2,272,481 | 2/1942 | Rinkes et al. | 128/66 |
| 2,415,455 | 2/1947 | Barnes et al. | 128/399 |
| 2,832,336 | 4/1958 | Davis et al. | 128/24.1 |
| 3,094,983 | 6/1963 | MacLeod | 128/40 |
| 3,186,404 | 6/1965 | Gardner | 128/87 |
| 3,901,225 | 8/1975 | Sconce | 128/402 |
| 3,918,458 | 11/1975 | Nethery | 128/400 |
| 3,967,627 | 7/1976 | Brown | 128/400 |
| 4,149,529 | 4/1979 | Copeland et al. | 128/24.1 |
| 4,338,944 | 7/1982 | Arkins | 128/400 |
| 4,370,975 | 2/1983 | Wright | 128/64 |
| 4,396,010 | 8/1983 | Arkans | 128/24.1 |
| 4,428,368 | 1/1984 | Torri | 128/24.1 |
| 4,453,538 | 6/1984 | Whitney | 128/82.1 |
| 4,574,812 | 3/1986 | Arkins | 128/691 |
| 4,773,397 | 9/1988 | Wright et al. | 128/40 |

FOREIGN PATENT DOCUMENTS 129481 12/1984 European Pat. Off. .............. 128/40

Primary Examiner—William H. Grieb
Assistant Examiner—Mark S. Graham
Attorney, Agent, or Firm—Carothers & Carothers

[57] ABSTRACT

A thermal applicator method using a support garment which encloses a human extremity such as an arm or a leg and includes a plurality of pockets adapted to receive thermal elements for retaining such thermal elements adjacent a specified portion of the human extremity and the combination of such a thermal applicator with a pressure applicator. The method comprises applying thermal treatment to a selected portion of the arm or leg and simultaneously applying a plurality of decreasing pressure steps the arm or leg from distal portions to proximal portions thereof.

1 Claim, 2 Drawing Sheets

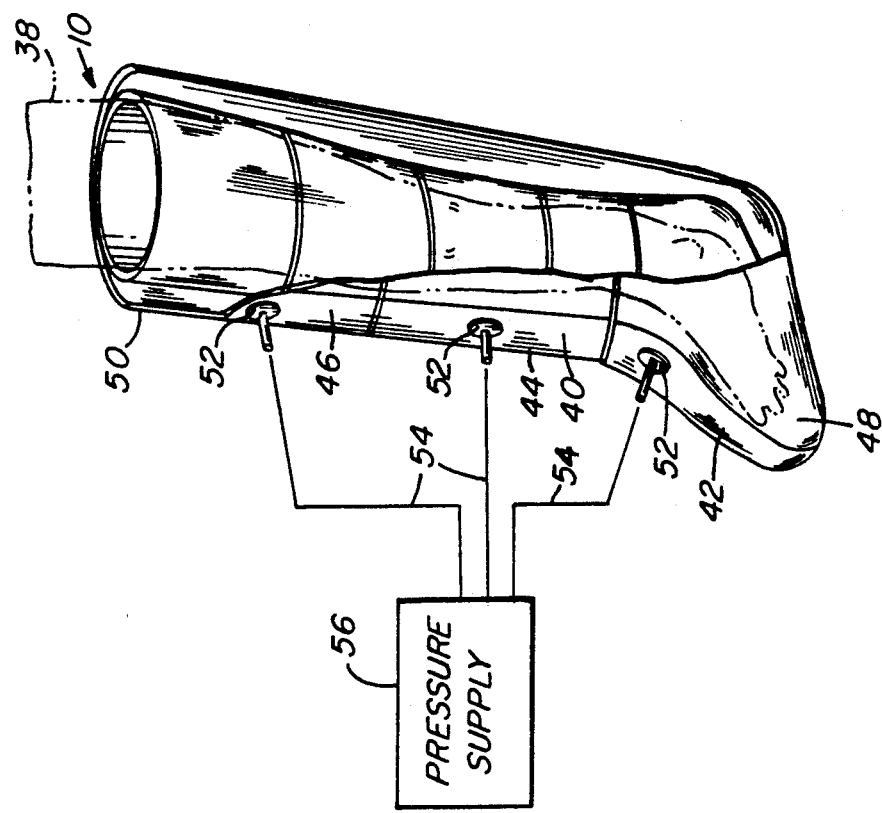
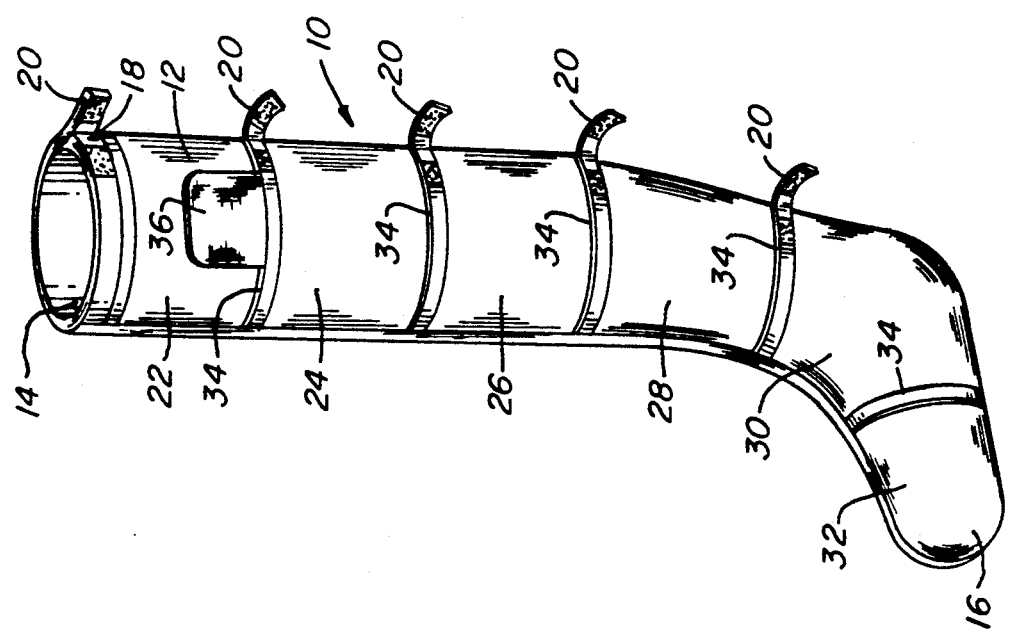

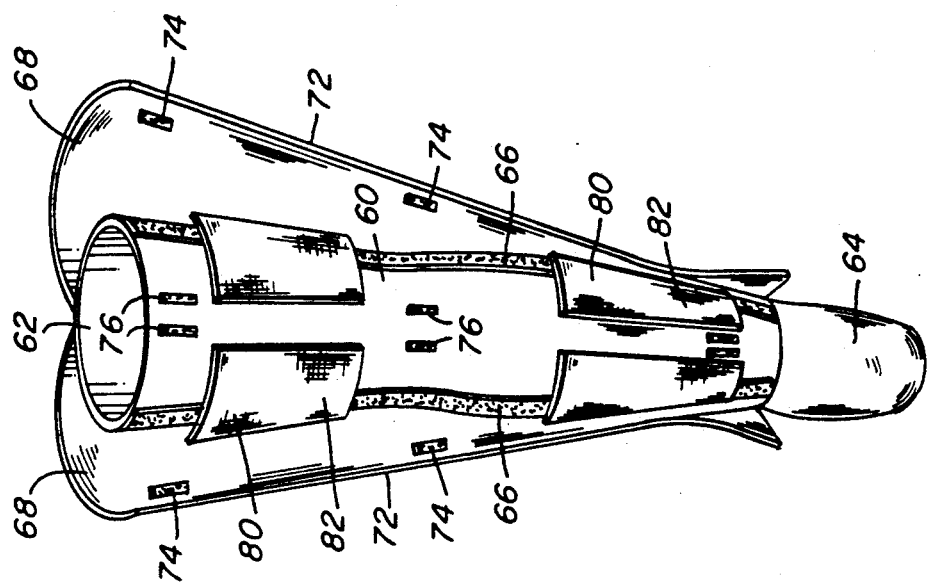
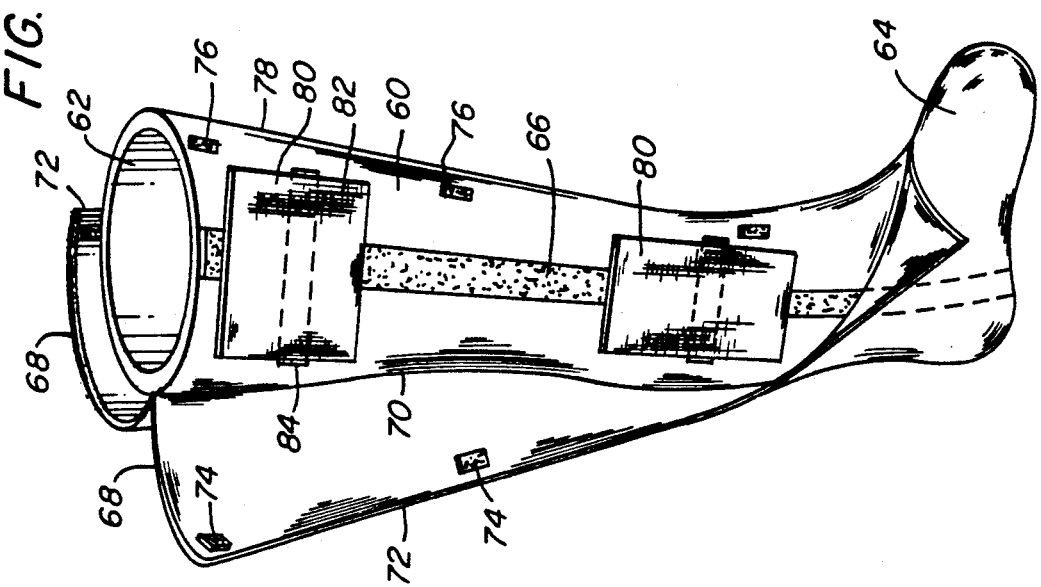

THERMAL APPLICATOR METHOD

BACKGROUND OF THE INVENTION

In the medical arts there are known a wide variety of devices for applying thermal environment externally to portions of a human body for the medical treatment thereof. For purposes of this application, the term "thermal" is intended to denote both hot and cold thermal application, thus, whirlpool baths, ice packs, hot water bottles, heating pads, and the like all are examples of such technology. Another is a hydrogel material which is sold under the trademark Elastogel.

In general, the placement of discrete thermal environment elements such as cold packs and hot water bottles or similar elements, and retention thereof with respect to a human extremity has posed significant difficulties. Accordingly, in the prior art it has been necessary to envelope the entire limb within a hot or cold thermal appliance even though the thermal environment was actually required only at a specific position or location to treat a corresponding specific portion of the limb. The application of thermal environment to an entire limb when only a localized portion required it is of course inefficient from the energy usage standpoint, but in addition it made for ineffective thermal environment therapy because for the typical patient the application of thermal environment to an entire limb, especially at temperatures varying widely from ambient temperature, quickly becomes very uncomfortable or even painful. The patient thus will not tolerate such application of thermal environment for long periods of time, and as a result the duration of thermal application therapy was necessarily limited.

There are also known garments in the nature of support stockings, wraps, and the like which are adapted to encompass a human extremity such as a leg or a portion thereof. Such support garments typically have been made from resilient elastic fabric or similar material to provide the requisite support function. The above and other expedients have been employed for various purposes including the treatment of circulatory deficiencies, contusions or bruises, muscle system and skeletal problems such as soreness or stiffness, as well as a variety of other conditions.

The art has further contemplated various sorts of apparatus for circulating thermal fluid through sleeves or other limb coverings which are adapted to enclose all or a portion of a human limb. Some such apparatus include pads or covers that are placed over a human limb and some include fluid chambers through which a heat transfer medium is pumped by a suitable pump apparatus to establish and maintain a desired temperature. Among the patents known to me which pertain generally to such apparatus are U.S. Pat. Nos. 4,338,994, 4,149,529, 3,967,627, 3,918,458, 2,415,455, 2,272,481, 3,186,404 and Italian patent 442,309.

Another prior art patent of interest regarding the present invention is U.S. Pat. No. 4,370,975, which discloses a sheath for receiving a human extremity such as an arm or leg, the sheath being divided into longitudinally spaced inflatable air cells encircling the limb, and a source of air pressure which is operable to inflate the respective cells to predetermined pressure magnitudes repeatedly in a timed sequence to produce a gradient pressure. The apparatus in this latter patent has been used for the treatment of lymph system disorders such as Parkes-Weber Syndrome which is characterized by the accumulation of lymphatic fluid in a human limb and resultant swelling of the limb to a much greater than normal size.

Notwithstanding the above and other expedients known in the prior art, practitioners of the art have continued to seek improved means of providing external application of thermal and/or pressure treatment to portions of the human body to treat a variety of disorders. Much recent activity in this regard has been undertaken in the sports medicine field, but medical practice in general is replete with examples of such treatments.

BRIEF SUMMARY OF THE INVENTION

The present invention contemplates a novel and improved method and apparatus for applying thermal treatment or simultaneous thermal treatment and pressure treatment to a human limb. In brief, the invention contemplates a stocking or similar garment, preferably of a stretch fabric or similar construction, for enclosing such a limb, and having a plurality of pockets which are adapted to retain thermal environment elements adjacent a corresponding selected portion or portions of the limb on which the stocking garment is worn. Judicious placement of the pockets or other retention means upon the stocking structure permits one or more thermal environment elements to be positioned at a location or locations selected by the medical practitioner to treat specific, selected portions of the limb.

The above characterized stocking may be utilized in conjunction with a pressure apparatus such as that disclosed in the above mentioned patent 4,370,975 by enclosing the human extremity in the novel stocking and then enclosing the stocking within the sheath of the pressure apparatus so that both thermal treatment and pressure may be applied simultaneously to such a human extremity. Specifically regarding the apparatus disclosed by U.S. Pat. No. 4,370,975, my invention further contemplates the combination of a stocking such as above characterized, and a pressure apparatus for applying gradient pressure repeatedly in timed sequence from a distal portion to a proximal portion of a human limb.

The invention thus provides a novel and improved apparatus and method for the application of thermal and pressure treatment to a human extremity. The advantages of the invention include but are not limited to enhanced ease and convenience in the application of thermal treatment, and improved patient tolerance of treatment. The invention also offers enhanced treatment modes by employing thermal treatment and gradient pressure simultaneously, and the same together with the static confining or supporting pressure of the stocking garment itself.

It is therefore one object of the invention to provide a novel and improved garment in the nature of a stocking or the like which is adapted to receive and retain thermal elements adjacent a predetermined, selected portion of a human extremity or limb.

A further object of the invention is to provide an apparatus and method for medical treatment comprised of static or stationary thermal treatment applied to a human extremity simultaneously with gradient pressure applied repeatedly in timed sequence from a distal portion to a proximal portion of the human extremity.

These and other objects and further advantages of the invention will be more readily appreciated upon consideration of the following detailed description and the accompanying drawings, in which:

BRIEF DESCRIPTION OF THE DRAWINGS

FIG. 1 shows a stocking garment according to one presently preferred embodiment of the instant invention in side elevation;

FIG. 2 shows the stocking of FIG. 1 enclosing a human leg and in turn being enclosed within a pressure sheath;

FIG. 3 is a side elevation of an alternative embodiment of the invention; and

FIG. 4 is a frontal elevation of the embodiment shown in FIG. 3.

DESCRIPTION OF THE PREFERRED EMBODIMENTS

There is generally indicated at 10 in FIG. 1 a stocking apparatus according to one presently preferred embodiment of the instant invention and comprising a generally hollow, tubular, elongated body 12 formed by stitching or similar construction from a flexible stretch fabric which exhibits the property of resilient elasticity, for example a blend of 54% lycra and 46% antron nylon.

The elongated tubular body 12 includes an open proximal end 14 and a closed distal end 16, although of course distal end 16 could alternatively be an open end if desired. In such form, the stocking 10 may be slipped endwise onto the leg of a user as shown in FIG. 2. Alternatively or in addition, stocking 10 may include a longitudinally extending opening 18 which extends substantially throughout the length thereof so that stocking 10 may be applied to the leg of a user by sliding the leg laterally into the opening 18 and thereafter securing the stocking by means of suitable closure or fastener elements 20, for example strips of interengaging hock and loop pile fastener material such as velcaotm brand fixed to stocking 10 adjacent the opposed sides of opening 18 at spaced intervals along the length thereof.

Along the length of stocking 10 there are disposed pockets which are adapted to receive thermal treatment elements such as cold compresses or heat retaining packets or pads. As shown, the pocket structure includes a plurality of pockets disposed serially from the upper open end 14 of stocking 10 and including an upper thigh pocket 22, a mid-thigh pocket 24, a knee pocket 26, a mid-calf pocket 28, an ankle pocket 30 and a foot pocket 32. A similar array of pockets may be disposed along the opposed lateral side of stocking 10, or in an alternative arrangement the pockets 22 through 32 inclusive may be smaller than as shown and similar arrays of smaller pockets may also be disposed along the front and rear of stocking 10 intermediate the laterally opposed series of side pockets.

Referring to pocket 24 as exemplary, each of the disclosed pockets includes an opening portion 34 through which a thermal treatment element 36 may be inserted into any selected one of the pockets 22-30. The thermal element 36 thus is retained adjacent a selected portion of the wearer's leg according to the pocket selected for its insertion, and thereby it provides the thermal energy source for hot or cold thermal treatment applied directly to a specific, selected portion of the user's leg.

Referring now to FIG. 2, the stocking 10 is shown enclosing a user's leg 38 and a pressure sheath 40 encloses the leg 38 and stocking 10. Sheath 40 includes a serial plurality of inflatable cell portions 42, 44 and 46 spaced longitudinally thereof from the distal end 48 to the proximal end 50 of sheath 40. Each cell 42, 44 and 46 is provided with a pressure conduit connection 52 for connection of a respective supply/exhaust conduit 54 extending from a pressure supply apparatus 56. The sheath 40, pressure supply 56 and connecting elements extending therebetween may be entirely similar in all salient respects to the apparatus disclosed in prior U.S. Pat. No. 4,370,975, especially as regards the operative ability of that apparatus to apply declining gradient pressure from the distal to the proximal end of a human extremity by repeated sequential inflation of the cells 42, 44 and 46 to specified pressure levels as disclosed in the cited prior patent. Reference is made hereby to said prior U.S. Pat. No. 4,370,975 for further detailed description, and the entire disclosure of said prior U.S. Pat. No. 4,370,975 is incorporated herein and made a part hereof by reference.

In an alternative embodiment of the invention as shown in FIGS. 3 and 4, a stocking garment 60 is fabricated from elastic material similar in all salient respects to that used for the stocking described hereinabove, and is made to generally conform to the shape of a human extremity such as an arm or leg, the leg stocking being shown at 60. A top opening 62 is provided for insertion of the limb into the stocking 60, and the opposed end 64 is enclosed. A wide band of fastener material 66, for example Velcrotm brand fastening material as disclosed hereinabove is attached to the opposed lateral sides of stocking 60 and extends substantially the entire length thereof.

Two wide flaps 68 are fixed adjacent a rear portion 70 of stocking 60 alongs a substantial extent of its length. The free edges 72 of the flaps 68 are provided with longitudinally spaced fasteners 74, for example Velcrotm brand fastener. Cooperating mating fastener elements 76 are affixed at spaced locations along a frontal portion 78 of stocking 60 whereby flaps 68 may be drawn over lateral side portions of stocking 60 and, by securing respective fastener elements 74 and 76, may enclose such lateral portions of stocking 60 entirely.

Thermal packs such as shown at 80 are covered with a lining material 82 such as antron nylon. A wide strip of fastener material 84 is disposed on one side of each pack 80 so as to extend lengthwise thereof intermediate its long edges, and is secured to the covering material 82 as by stitching, for example. The fastener material 84 is compatible with material 66 for securing packs 80 with respect to stocking garment 60 at any selected position along the extent of fastener material 66. In addition, by orienting the fastener material 66 and 84 generally at right angles, the position of the packs 80 also may be adjusted toward the frontal or rear portions of stocking 60. This allows for continuously adjustable horizontal and vertical placement of the packs 80, depending upon the application position needed in the judgement of the medical practitioner.

After positioning the pack or packs 80 as described, flaps 68 are drawn over the lateral sides of stocking 60 and the retained packs 80 and secured thereabout by fasteners 74, 76. The flaps 68 thus assist in retaining packs 80 in the desired position.

Maintaining packs 80 in the selected position by means of flaps 68, or the pockets disclosed hereinabove with reference to FIGS. 1 and 2, is important as the thermal environment packs must be retained in the desired position upon insertion of the limb with stocking and thermal packs into the sheath of a pressure apparatus such as shown in FIG. 2. It will be understood that the stocking garment 60 of FIGS. 3 and 4 may be used in conjunction with a pressure appliance such as shown in FIG. 2 in entirely the same manner as above described with respect to the stocking garment of FIG. 1.

From the above description, the method of my invention will be understood to comprise the steps of enclosing a human limb in a thermal treatment garment or appliance, retaining a static thermal treatment element adjacent a specific selected portion of the limb and applying the thermal effect of the thermal treatment element to the respective portion of the limb. The method of my invention further contemplates the above steps in combination with the simultaneous application of pressure to the limb, preferably in a pressure application mode which includes a declining or decreasing gradient pressure applied from a distal portion to a proximal portion of the limb with the gradient pressure steps being applied in timed sequence beginning with the larger magnitude pressure steps and ending with the lower magnitude pressure steps of the pressure gradient.

From the above description it will be seen that I have invented a novel and improved apparatus and method for medical treatment of a human extremity. Of course, I have contemplated various alternative and modified embodiments of the invention and such would certainly also occur to others versed in the art once apprised of my invention. Accordingly, it is intended that the invention should be construed broadly in accordance with the scope of the claims appended hereto.

I claim:

1. In the medical treatment of a human body, a method of treating a given portion of a human extremity wherein said given portion includes relatively distal and proximal regions comprising the steps of:

subjecting said given portion of said extremity to externally applied pressure;

simultaneously with said subjecting step, applying thermal treatment to only a selected localized part of said given portion; and during said simultaneous applying and subjecting steps, periodically varying the magnitude of said externally applied pressure to apply a plurality of decreasing pressure steps in timed sequence in a manner to subject said given portion to a pressure gradient which decreases from said relatively distal region to said relatively proximal region.

* * * * *